US012723254B2

(12) United States Patent
Shao et al.

(10) Patent No.: US 12,723,254 B2
(45) Date of Patent: Sep. 1, 2026

(54) **HD-ZIP TRANSCRIPTION FACTOR ArHDZ19 OF *Anoectochilus roxburghii* HONGXIA, ENCODING GENE AND USE OF ENCODING GENE**

(71) Applicant: Zhejiang A&F University, Hangzhou (CN)

(72) Inventors: Qingsong Shao, Hangzhou (CN); Yu Zhang, Hangzhou (CN); Taowei Zhong, Hangzhou (CN); Aimin Lv, Hangzhou (CN)

(73) Assignee: Zhejiang A&F University, Hangzhou (CN)

( * ) Notice: Subject to any disclaimer, the term of this patent is extended or adjusted under 35 U.S.C. 154(b) by 73 days.

(21) Appl. No.: 18/888,245

(22) Filed: Sep. 18, 2024

(65) Prior Publication Data

US 2025/0243503 A1 Jul. 31, 2025

(30) Foreign Application Priority Data

Jan. 26, 2024 (CN) ........................ 202410111910.0

(51) Int. Cl.
*C12N 15/82* (2006.01)
*C07K 14/415* (2006.01)

(52) U.S. Cl.
CPC ........ *C12N 15/8267* (2013.01); *C07K 14/415* (2013.01); *C12N 15/8205* (2013.01)

(58) Field of Classification Search
CPC ............ C12N 15/8267; C12N 15/8205; C12N 15/8261; C07K 14/415
See application file for complete search history.

(56) References Cited

U.S. PATENT DOCUMENTS 9,896,695 B2 * 2/2018 Chan .................. C12N 15/8261

OTHER PUBLICATIONS

Huang, Hui, et al. "Identification and characterization of HD-Zip genes reveals their roles in stresses responses and facultative crassulacean acid metabolism in Dendrobium catenatum." Scientia Horticulturae 285 (2021): 110058., published Mar. 5, 2021 (Year: 2021).*

XP_020698923.1, homeobox-leucine zipper protein HOX32 [Dendrobium catenatum], 2019, retrieved from https://www.ncbi.nlm.nih.gov/protein/XP_020698923.1 (Year: 2019).*

XP_020698923.1, homeobox-leucine zipper protein HOX32 [Dendrobium catenatum], 2019, retrieved from: https://www.ncbi.nlm.nih.gov/protein/XP_020698923.1.

* cited by examiner

*Primary Examiner* — Bratislav Stankovic
*Assistant Examiner* — Yvette B. Tamukong
(74) *Attorney, Agent, or Firm* — Bayramoglu Law Offices LLC

(57) ABSTRACT

An HD-ZIP transcription factor ArHDZ19 of *Anoectochilus roxburghii* 'Hongxia', encoding gene, and use of encoding gene are provided. The transcription factor ArHDZ19 includes a polypeptide having the amino acid sequence as shown in SEQ ID NO: 2. A gene for encoding the above-mentioned proteins having the nucleotide sequence as shown in SEQ ID NO: 1 is provided. The present invention provides a theoretical basis for using genetic engineering technology to promote the reproductive growth of *Anoectochilus roxburghii* 'Hongxia' and improve seed vitality, and has important application value.

6 Claims, 7 Drawing Sheets

Specification includes a Sequence Listing.

FIG. 4
CK
OE-*ArHDZ19*
OE-*ArHDZ19*
OE-*ArHDZ19*

HD-ZIP TRANSCRIPTION FACTOR ArHDZ19 OF *Anoectochilus roxburghii* HONGXIA, ENCODING GENE AND USE OF ENCODING GENE

CROSS REFERENCE TO THE RELATED APPLICATIONS

This application is based upon and claims priority to Chinese Patent Application No. 2024101119100, filed on Jan. 26, 2024, the entire contents of which are incorporated herein by reference.

SEQUENCE LISTING

The instant application contains a Sequence Listing which has been submitted in XML format via EFS-Web and is hereby incorporated by reference in its entirety. Said XML copy is named GBJSQT007_SequenceListing_20260306.xml, created on Mar. 6, 2026, and is 11,682 bytes in size.

TECHNICAL FIELD

The present invention belongs to the technical field of genetic engineering application, and relates to an important homeodomain-leucine zipper (HD-ZIP) protein in the reproductive growth process of *Anoectochilus roxburghii*, and in particular to an HD-ZIP transcription factor ArHDZ19 of *Anoectochilus roxburghii* 'Hongxia', an encoding gene of the ArHDZ19, and a use of the encoding gene.

BACKGROUND

*Anoectochilus roxburghii* (*Anoectochilus roxburghii* (Wall.) Lindl.), also known as Jinsicao and Jinxianlan in Chinese, is a perennial herb of the genus *Anoectochilus* of the Orchidaceae family and also a rare and precious Chinese medicinal material. It tastes sweet and has a neutral nature, and the whole plant of *Anoectochilus roxburghii* can be used for medicinal purpose, with the effects of clearing heat, cooling blood, removing dampness and toxic material, thereby earning the reputation of "King of Medicine". In recent years, the wide application of *Anoectochilus roxburghii* in many fields has led to an increasing demand in the Chinese and international markets. However, the pollen and stigma of *Anoectochilus roxburghii* are viable for a short period of time, and the natural reproduction rate of seeds is low. The seeds of *Anoectochilus roxburghii* have embryo abortion after fertilization, resulting in reproductive disorders in *Anoectochilus roxburghii*.

Homeodomain-leucine zipper (HD-ZIP) proteins are a class of transcription factors unique to higher plants. They participate in plant-specific biological processes and play an important role in the growth and development of higher plants. HD-ZIP III subfamily transcription factors participate in regulating the reproductive development of plants and are closely related to the embryonic and post-embryonic morphogenesis, cell differentiation, lateral organogenesis, vascular cell division, and polarity establishment of plants. However, there are no reports on the involvement of HD-ZIP proteins in the reproductive development of *Anoectochilus roxburghii*.

SUMMARY

In order to fill the gaps in the research on the cloning and expression pattern of the ArHDZ19 gene of *Anoectochilus roxburghii* 'Hongxia' and the transcription factor ArHDZ19 of *Anoectochilus roxburghii* 'Hongxia', the present invention provides an ArHDZ19 gene sequence of a HD-ZIP of *Anoectochilus roxburghii* 'Hongxia' and the encoded amino acid sequence, protein subcellular localization, and transgenic plant growth phenotype thereof, thereby providing a theoretical basis for using genetic engineering technology to regulate the expression of the ArHDZ19 gene and improve the breeding efficiency of *Anoectochilus roxburghii* in the future.

In one aspect, the present invention provides an HD-ZIP transcription factor ArHDZ19 of *Anoectochilus roxburghii* 'Hongxia', having the function of promoting reproductive development and improving seed traits. The transcription factor ArHDZ19 includes a polypeptide (protein) having an amino acid sequence as shown in SEQ ID NO: 2; or a protein having the characteristics of the HD-ZIP transcription factor ArHDZ19 of *roxburghii* 'Hongxia' and obtained by replacement, deletion or addition of one or more amino acids on the amino acid sequence shown in SEQ ID NO: 2.

In another aspect, the present invention provides an encoding gene for encoding the HD-ZIP transcription factor ArHDZ19 of *Anoectochilus roxburghii* 'Hongxia', and the nucleotide sequence of the encoding gene is specifically: (a) a base sequence from positions 1 to 2553 as shown in SEQ ID NO: 1; or (b) a sequence having at least 70% homology with nucleic acids at positions 1 to 2553 as shown in SEQ ID NO: 1.

In the present invention, the terms "isolated DNA" and "purified DNA" mean that the DNA or fragment has been isolated from the sequences located on two sides of it in a natural state, and also mean that the DNA or fragment has been separated from the components accompanying the nucleic acid in the natural state, and has been separated from the proteins accompanying it in the cell.

In the present invention, the encoding gene of the HD-ZIP transcription factor ArHDZ19 of *Anoectochilus roxburghii* 'Hongxia' refers to a nucleotide sequence that encodes a polypeptide having the protein activity of the *Anoectochilus roxburghii* 'Hongxia', such as the nucleotide sequence from positions 1 to 2553 shown in SEQ ID NO: 1 and its degenerate sequence. The degenerate sequence refers to a sequence generated after one or more codons in nucleotides at positions 1 to 2553 shown in SEQ ID NO: 1 are replaced by degenerate codons encoding the same amino acid. Due to the degeneracy of codons, a degenerate sequence with a homology of as low as about 70% with the nucleotide sequence from positions 1 to 2553 shown in SEQ ID NO: 1 can also be encoded to obtain the sequence shown in SEQ ID NO: 2. The described encoding gene may also refer to a nucleotide sequence having at least 70% homology with the nucleotide sequence shown in SEQ ID NO: 1.

The described encoding gene may also refer to being capable of encoding a variant form of the sequence shown in SEQ ID NO: 1 that has the same function as the natural HD-ZIP transcription factor ArHDZ19 of *Anoectochilus roxburghii* 'Hongxia', and these variant forms include (but are not limited to): usually a deletion, insertion and/or substitution of 1 to 120 nucleotides, and an addition of less than 120 nucleotides at the 5' and/or 3' ends.

In the present invention, real-time fluorescence quantitative PCR may be used to analyze the expression pattern of the product of the ArHDZ19 gene of *Anoectochilus roxburghii* 'Hongxia', that is, to analyze the presence and quantity of the mRNA transcripts of the ArHDZ19 gene of *Anoectochilus roxburghii* 'Hongxia' in the cells.

In addition, according to the nucleotide sequence and amino acid sequence of the ArHDZ19 gene of *Anoectochilus roxburghii* 'Hongxia' of the present invention, homologous genes or homologous proteins related to the ArHDZ19 gene of *Anoectochilus roxburghii* 'Hongxia' can be screened on the basis of the homology of nucleic acids or the homology of expressed proteins.

The relevant full-length nucleotide sequence of the ArHDZ19 gene of *Alocasia roxburghii* 'Hongxia' of the present invention or fragments thereof can usually be obtained by means of PCR amplification, recombination or artificial synthesis. For PCR amplification, primers may be designed according to the relevant nucleotide sequence disclosed in the present invention, and a commercially available cDNA bank or a cDNA bank prepared by a conventional means known to those skilled in the art can be used as a template for amplification to obtain a relevant sequence. When the sequence is long, PCR amplification may be performed twice or more, and then the fragments obtained after the amplifications are spliced together in a correct order.

Once the relevant sequence is obtained, a large quantity of the relevant sequence may be obtained by means of recombination. This is usually done by cloning the relevant sequence into a vector, and then transferring it into a cell, and finally isolating the relevant sequence from proliferated host cells by conventional methods.

In addition, mutations may also be introduced into the protein sequence of the present invention by chemical synthesis.

In addition to being produced by means of recombination, fragments of the protein of the present invention may also be produced by direct peptide synthesis using a solid phase technology. Each fragment of the protein of the present invention can be chemically synthesized separately and then chemically linked to produce a full-length molecule.

The present invention further provides a recombinant expression vector, which includes the encoding gene of the described HD-ZIP transcription factor ArHDZ19 of *Anoectochilus roxburghii* 'Hongxia'. The described recombinant expression vector is pHB-ArHDZ19.

The present invention further provides a use of the encoding gene of the HD-ZIP transcription factor ArHDZ19 of *Anoectochilus roxburghii* 'Hongxia' in promoting the reproductive growth of *Anoectochilus roxburghii* and improving the seed vitality.

The use described above includes: constructing a recombinant expression vector including the described encoding gene of the described transcription factor ArHDZ19, transforming a plant host, and performing cultivation and screening to obtain a transgenic plant.

As a rare and precious Chinese medicinal material, *Anoectochilus roxburghii* has a large market demand. In the present invention, the encoding sequence of the important regulatory transcription factor ArHDZ19 in the growth and development process of *Anoectochilus roxburghii* 'Hongxia' is cloned for the first time, the expression pattern of the ArHDZ19 gene is analyzed by means of real-time fluorescence quantitative PCR, and the subcellular localization of the transcription factor ArHDZ19 is analyzed by transient expression in epidermal cells of tobacco leaves, thereby laying a theoretical basis for regulating the spatiotemporal expression of the ArHDZ19 gene by genetic engineering technology in the future to improve the vitality of *Anoectochilus roxburghii* seeds, promote reproductive growth, and breeding new varieties, and also achieving a great application value.

BRIEF DESCRIPTION OF THE DRAWINGS

(FIG. 1A) Diagram of evolutionary tree analysis of ArHDZ19 protein and homologous proteins in other species. (FIG. 1B) Diagram of alignment of multiple sequences.

(FIG. 5A) Schematic diagram of the seed traits of the wild-type plant. (FIG. 5B) Schematic diagram of the seed traits of the OE-ArHDZ19 plant. (FIG. 5C) Schematic diagram of hundred-grain weight of seeds. (FIG. 5D) Schematic diagram of seed length.

DETAILED DESCRIPTION OF THE EMBODIMENTS

Figure 1A:
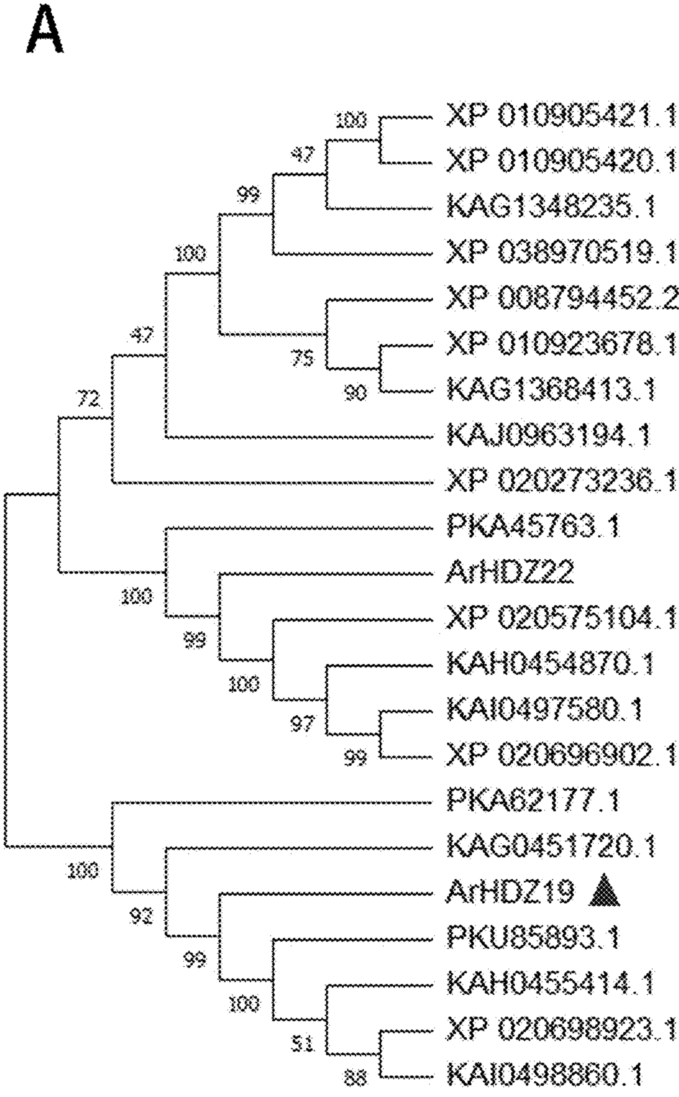
FIGS. 1A-1B shows the homology comparison (DNAMAN) between an HD-ZIP gene of *Anoectochilus roxburghii* 'Hongxia' and an HD-ZIP protein sequence of *Arabidopsis thaliana* and the evolutionary tree analysis of homologous genes.

The present invention will be further described below with reference to specific examples. It should be understood that these examples are only for illustrating the present invention and are not intended to limit the scope of the present invention.

Experimental methods without specific conditions listed in the following examples are generally conducted under conventional conditions, such as those described in Molecular Cloning: A Laboratory Manual (Fourth Edition), or the conditions suggested in the reagent instructions.

Example 1 Cloning of ArHIDZ19 Gene of *Anoectochilus roxburghii* 'Hongxia'

1. Acquisition of Plant Materials

Tissues, such as stems, leaves, buds, and flowers, of normally growing *Anoectochilus roxburghii* 'Hongxia' plants were taken to extract total RNA.

2. Extraction of RNA

The total RNA was extracted using a "TransZol Up Plant Total RNA Extraction Kit" (Beijing TransGen Biotech Co., Ltd), and the integrity of the RNA was identified by gel electrophoresis. The purity and concentration of the RNA were determined by a spectrophotometer (Nanodrop 2000).

3. Full-Length Cloning of the Gene

Based on the nucleotide sequence and protein function annotation results provided by the laboratory's previous full-length transcriptome analysis, the full-length ArHDZ19 gene of *Anoectochilus roxburghii* 'Hongxia' was obtained. The extracted RNA was reverse transcribed (TransScript One-Step gDNA Removal and cDNA Synthesis SuperMix) to obtain cDNA. A first-strand cDNA, used as a template, was subjected to PCR amplification using primers ArHDZ19-F (5'-ATGGCGATGATGGTGAGCGC-3') and ArHDZ19-R (5'-TCAAACAAAAGACCAGTTGATGATCATAA-3') to obtain a 2553 bp fragment. The fragment was recovered and linked to a pMD19-T vector and then delivered to Hangzhou Youkang for sequencing with M13-47 and RV-M as universal primers.

By combining the sequencing results with the prediction from the ORF Finding of NCBI (www.ncbi.nlm.nih.gov/gorf), the ORFs (Open Reading Frames) of the ArHDZ19 gene of *Anoectochilus roxburghii* were found, and then the full-length encoding sequence with a length of 2553 bp (SEQ ID NO: 1) was obtained by amplification. The sequencing results were compared with the database (GenBank, blast.ncbi.nlm.nih.gov/) using BLAST on the NCBI website. Its nucleotide sequence and encoding protein had a high homology with the known DcHD-Zip III (XP_020698923.1) nucleotide and protein sequences of Dendrobium *officinale*. So it was initially considered to be an HD-ZIP gene.

Example 2 Sequence Information and Homology Analysis of the ArHDZ19 Gene of *Anoectochilus roxburghii* 'Hongxia'

The full-length ORF sequence of the ArHDZ19 gene of *Anoectochilus roxburghii* 'Hongxia' of the present invention is 2553 bp. For the detailed sequence, please refer to the sequence shown in SEQ ID NO: 1. The amino acid sequence of the transcription factor ArHDZ19 protein of *Anoectochilus roxburghii* 'Hongxia', with a total of 850 amino acids, a molecular weight of 93.4 kDa, and an isoelectric point (pI) of 8.19, was deduced from the ORF sequence. For the detailed sequence, please refer to the sequence shown in SEQ ID NO: 2.

Figure 1B:
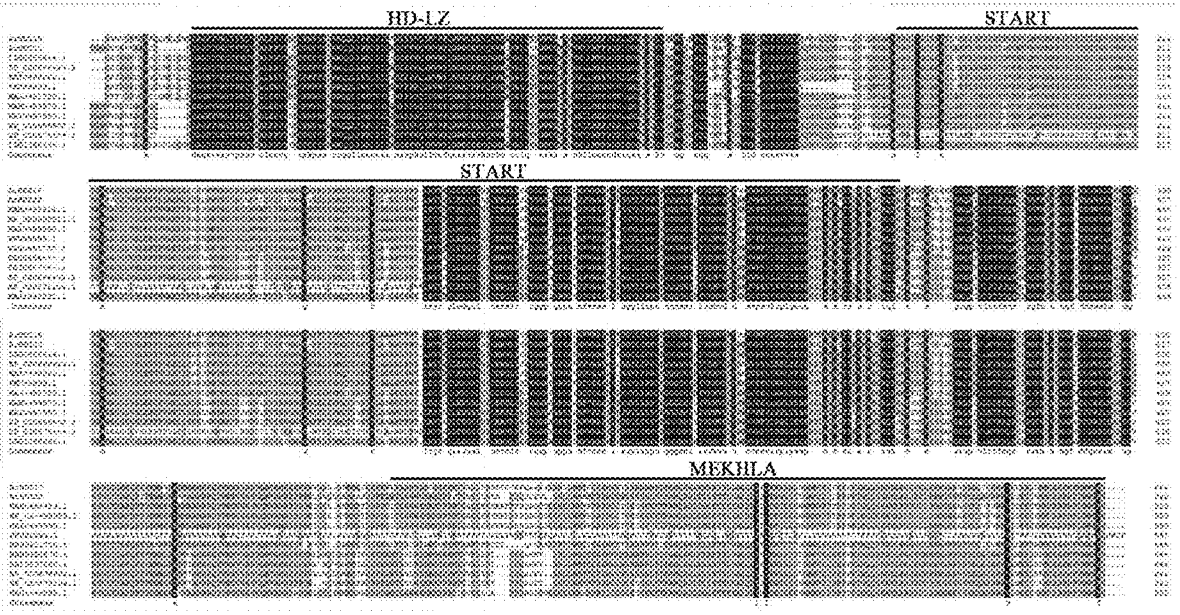

The ORF sequence of the ArHDZ19 gene of *Anoectochilus roxburghii* 'Hongxia' and the amino acid sequence of its encoding protein were searched for nucleotide and protein homology in NCBI using the BLAST program. The results showed that the transcription factor ArHDZ19 of *Anoectochilus roxburghii* 'Hongxia' had a very high homology with DcHD-Zip III (XP_020698923.1) of Dendrobium *officinale* at the amino acid level, as shown in FIG. 1B. Evolutionary tree analysis showed that the transcription factor ArHDZ19 of *Anoectochilus roxburghii* 'Hongxia' had a high homology with HD-ZIP proteins of other known species, as shown in FIG. 1A.

Example 3 Construction of Recombinant Expression Vector pHB-ArHDZ19 of *Anoectochilus Roxburghii* and Analysis of Subcellular Localization of the Transcription Factor ArHDZ19 in Tobacco Leaves Specific primers ArHDZ19-F (5'-TCGGTACCCGGGGATCCATGGCGATGGTGGGGAAGGA-3') (SEQ ID NO: 3) and ArHDZ19-R (5'-TGCTCACCATGTCGACGACAAATGACCAGTTCATGAAC-3') (SEQ ID NO: 4) were designed respectively from the start codon and the stop codon, and BamHI and SpeI restriction sites were introduced on two sides of the full-length gene sequence. The target fragment plasmid with restriction sites and the pHB binary transformation vector were double-digested with BamHI and SpeI, the pHB vector after restriction digestion and the ArHDZ19 fragment were recovered and linked by T4 ligase at 16° C. for 6 h to construct the recombinant expression vector pHB-ArHDZ19.

Figure 2:
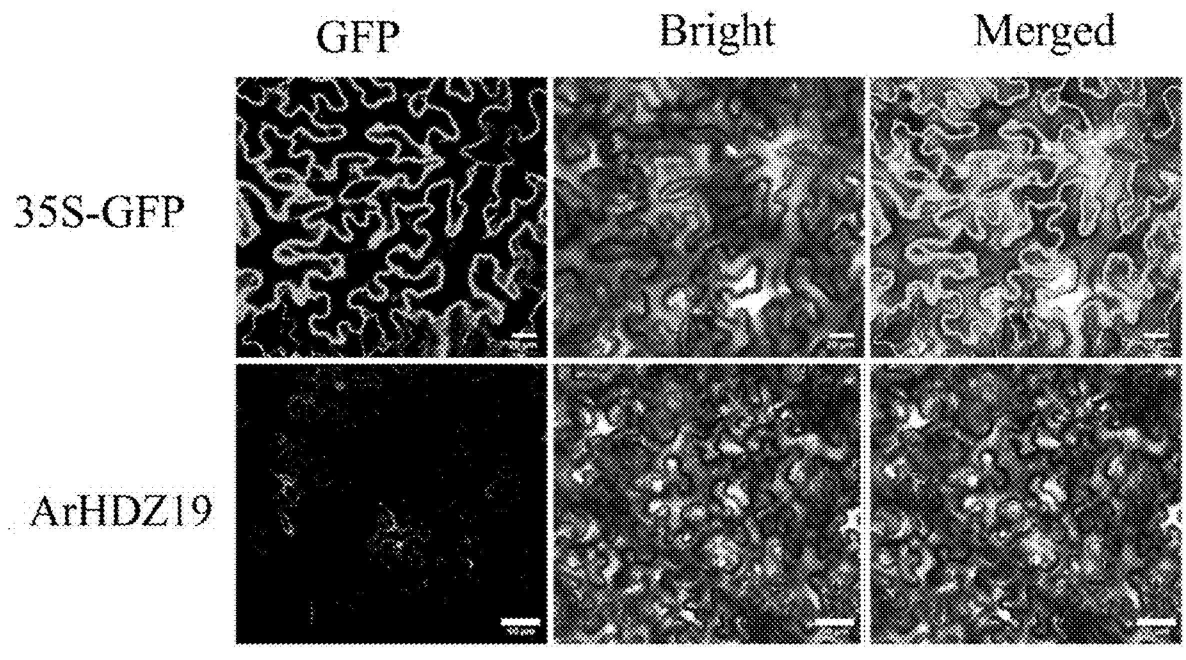
FIG. 2 is a localization diagram of the transcription factor ArHDZ19 of *Anoectochilus roxburghii* 'Hongxia' in the epidermal cells of tobacco leaves.

The recombinant expression vector pHB-ArHDZ19 which was identified to be correct was transformed into *Agrobacterium* EHA105. The identified EHA105 strain was inoculated in 5 mL of YEP (containing 50 mg/L Kan), and cultured at 28° C. and 180 rpm until OD600 was about 0.6; 1 mL of the culture solution was taken and added to 25 mL of YEP liquid medium, and cultured at 28° C. until OD600 was about 0.6; 10 mL of the culture solution was taken and centrifuged at 4500 rpm for 15 min; the bacteria were then suspended in an MS liquid medium until OD600 was about 0.6, AS and MES were then added, and the suspension was then placed at room temperature for more than 3 h; then, the suspension was injected into tobacco leaves, cultured in the dark for 48 h, and observed under a laser confocal microscope at an excitation wavelength of 514 nm, as shown in FIG. 2.

Example 4 Expression Changes of ArHDZ19 Gene of *Anoectochilus roxburghii* in Different Tissues of *Anoectochilus roxburghii*

Figure 3:
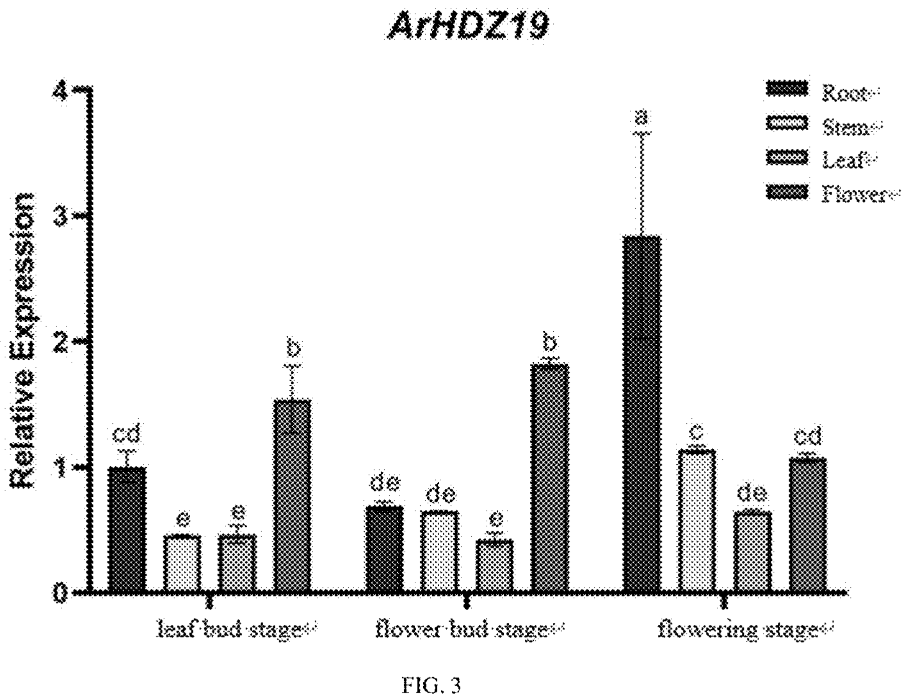
FIG. 3 shows expression changes of the ArHDZ19 gene of *Anoectochilus roxburghii* 'Hongxia' during the growth and development of plants.

1. Acquisition of materials: Root, stem, leaf and flower tissue samples at different developmental stages (leaf bud stage, flower bud stage and flowering stage) during the growth of *Anoectochilus roxburghii* plants were taken, each 0.1 g. The samples were wrapped with aluminum platinum paper separately and put into liquid nitrogen, then transferred to an −80° C. ultra-low temperature refrigerator for storage.
2. The extraction of RNA, the integrity, purity and concentration determination of RNA and the acquisition of cDNA were performed with reference to Example 1.
3. Specific primers were designed to perform real-time fluorescence quantitative PCR to analyze the expression of the gene in various tissues. The specific primers, designed for quantitative analysis of ArHDZ19 gene in Real-time PCR according to the obtained ArHDZ19 gene sequence of *Anoectochilus roxburghii*, included the primer qArHDZ19-F (5'-GTATACGCCGGAGCAAGTGG-3') (SEQ ID NO: 5) and the primer qArHDZ19-R (5'-TCTCTGATGAGCTGCTGCCT-3') (SEQ ID NO: 6), as well as the primers for the internal reference gene actin which were actin-F (5'-GCTAGTGGCCGTACAACTGG-3') (SEQ ID NO: 7) and actin-R (5'-GCCAGCAAGGTCCAATCGAA-3') (SEQ ID NO: 8).
4. Standard curves of the target gene and the internal reference gene: The standard cDNA solution was diluted with $ddH_2O$ in a gradient manner; the diluted cDNA, used as a template, was subjected to real-time PCR amplification using the specific primers of the target gene and the internal reference gene, and then a melting curve and a standard curve were plotted. The melting curve was analyzed to determine whether the melting curve of the target gene and the internal reference gene has a single peak, so as to determine whether a single PCR amplification product can be obtained using the primers; and the appropriate dilution multiple of the template cDNA was determined according to the standard curve.
5. Real-time fluorescence quantitative analysis of the target gene in the samples to be tested: The first strand of synthesized cDNA, used as a template, was subjected to amplification using specific primers of the target gene and the internal reference gene to conduct fluorescence quantitative analysis. Real-time PCR was performed using a Bio-Rad CFX real-time fluorescence quantification instrument, where the reaction system was 20 μL, and the reaction procedure was: pre-denaturation at 94° C. for 20 s, 94° C. for 15 s; 55° C. for 15 s; 72° C. for 15 s; 40 cycles.
6. The 2-ΔΔCt method was used for relative quantitative analysis. The results showed that the expression level of the ArHDZ19 gene of *Anoectochilus roxburghii* increased significantly in *Anoectochilus roxburghii* tissues at different development stages, as shown in FIG. 3.

Example 5 ArHDZ19 Gene Transformation of *Arabidopsis thaliana*

1. Construction of Plant Expression Vector

For the introduced restriction sites, please refer to Example 3. The target fragment plasmid with restriction sites and the pHBB binary transformation vector were double digested with BamHI and SpeI, the vector after restriction digestion was recovered and linked by means of homologous recombination, and the recombinant expression vector was then transformed into *Agrobacterium* EHA105.

2. Transformation of *Arabidopsis thaliana*

Transformation of *Arabidopsis thaliana* by flower infection: The operation of infecting *Arabidopsis thaliana* by *Agrobacterium*-mediated inflorescence immersion was specifically performed as follows.

① When wild-type *Arabidopsis thaliana* grew to the middle and early flowering period, the best period for infection of *Arabidopsis thaliana* was reached. The blooming flowers and fruit pods were cut off one day before infection, and the flowers in buds were remained and were given plenty of water and fertilizer to get ready for infection.

② 100 μL of positive *Agrobacterium* culture was taken and expanded in 25 mL of LB liquid medium containing Kana (50 mg/L) and Rif (25 mg/L). The culture was then shaken in a constant-temperature shaker (28° C., 220 rpm) until the OD600 of the culture reached 0.8-1.0.

③ When the OD600 of the expanded *Agrobacterium* culture reached 0.8-1.0, centrifugation was performed at 6000 rpm for 10 min to collect the bacteria, and the supernatant was discarded.

④ The bacteria were suspended with an MS resuspension solution (4.43 g/L MS powder+20 g/L sucrose, pH 5.8) and the OD600 was adjusted to 0.8-1.0. Then, Tween-20 was added to control the final concentration at 0.02%, and the suspension was then well shaken, thus obtaining the infection solution.

⑤ Inflorescences of each *Arabidopsis thaliana* plant was soaked completely in the infection solution for 10 min.

⑥ After the infection, the *Arabidopsis thaliana* plants were bagged and placed flat in a dark room for dark culture for 1 day to maintain humidity. After the dark culture, the *Arabidopsis thaliana* plants were placed in a greenhouse with a temperature of 22° C. and a humidity of 65% to be cultured normally for 16 h with light and 8 h in the dark each day.

⑦ One week later, the described operations were repeated to infect *Arabidopsis thaliana* again to increase the success rate of transformation.

⑧ After the second infection, the *Arabidopsis thaliana* was cultured normally and managed in the conventional cultivation method until harvest.

3. Screening of Positive Transgenic Lines

Genomic DNA and RNA were extracted using the kit (Beijing TransGen Biotech Co., Ltd) to identify positive plants.

Example 6 Phenotypic Analysis of OE-ArHDZ19 *Arabidopsis thaliana*

The objects selected for phenotypic observation and measurement of *Arabidopsis thaliana* were positive homozygous T3 plants and positive homozygous T3 seeds (OE), and *Arabidopsis thaliana* transformed with pHB empty vector was used as negative control (CK). The indicators for phenotypic observation and measurement were: plant growth cycle, plant height, seed length and width, and hundred-grain weight of seeds.

Figure 4:
FIG. 4 shows growth and development phenotypes of wild-type and OE-ArHDZ19 plants.
Figure 5A:
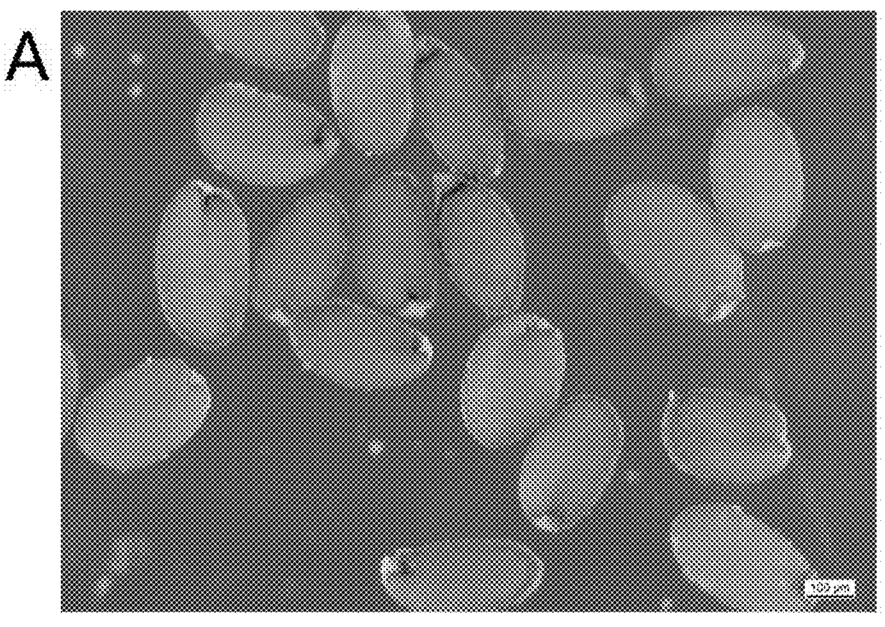
FIGS. 5A-5D show seed traits of the wild-type and OE-ArHDZ19 plants.
Figure 5B:
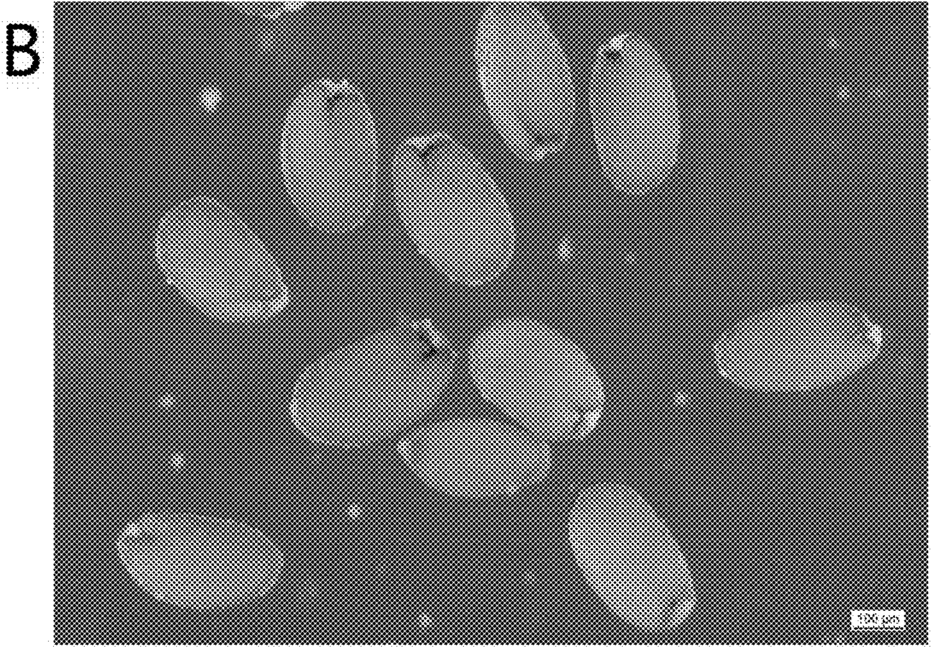
Figure 5C:
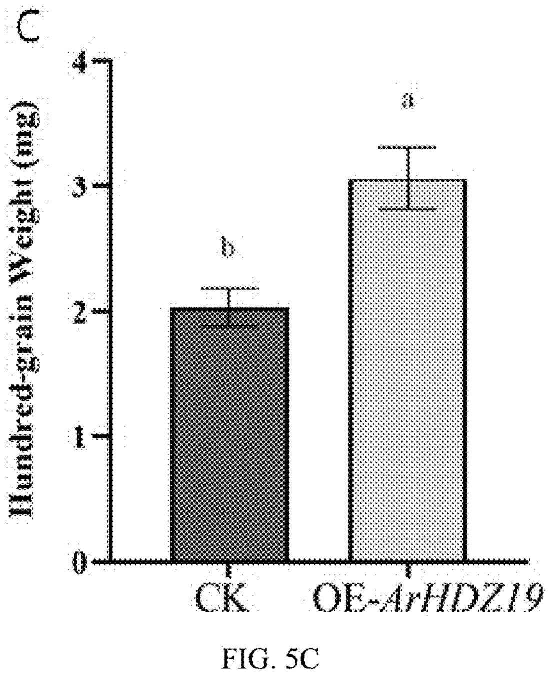
Figure 5D:
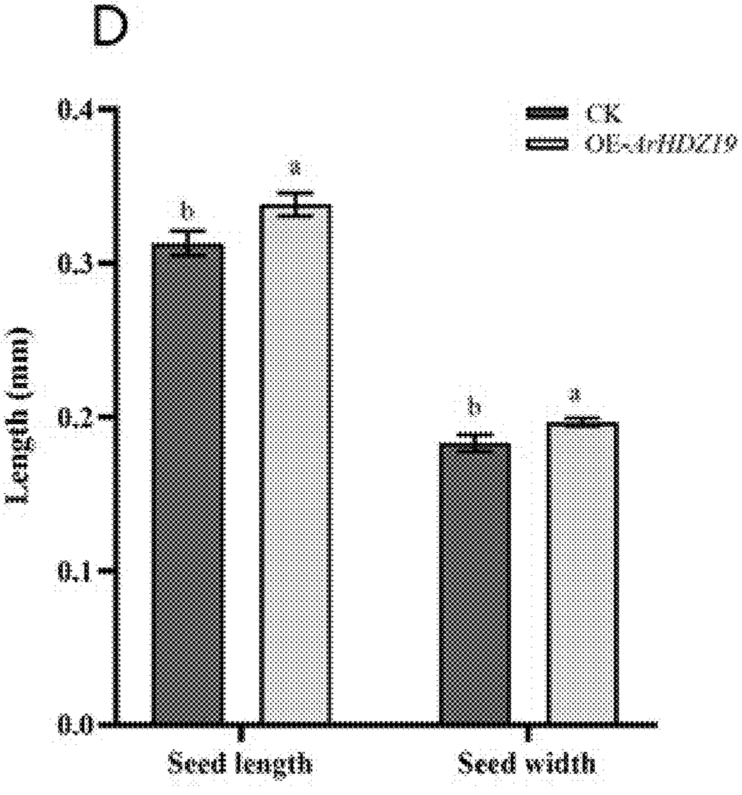

Method for observing plant growth cycle: Three *Arabidopsis thaliana* plants were randomly selected from transgenic plants on day 37 after sowing, and the difference in growth cycle between the selected plants and control plants was observed and recorded in the form of photos. Method for measuring plant height: On day 44 after sowing, three *Arabidopsis thaliana* plants were randomly selected from control plants and three *Arabidopsis thaliana* plants were randomly selected from transgenic plants, and these selected plants were taken out of pots with the cultivation medium washed off, and then placed on black cloth to measure the distance from the base of the rosette leaf to the top of the inflorescence and photographed, as shown in FIG. 4.

Method for measuring seed length and width: Several control plant seeds and transgenic plant seeds were selected and randomly spread on a glass slide, and then observed under an optical microscope and photographed under natural light. Then, ten seeds were randomly selected from the field of view to calculate the average length and width using a scale. Method for measuring hundred-grain weight of seeds: 100 seeds from the control plants and 100 seeds from transgenic plants were weighed on an analytical balance respectively, as shown in FIGS. 5A-5D.

The above describes the specific embodiments of the invention. It should be understood that the invention is not limited to the above specific embodiments, those skilled in the art can make various modifications or changes within the scope of the claims, and these modifications or changes do not affect the essence of the invention.

What is claimed is:

1. A transgenic plant, comprising a recombinant expression vector, wherein the recombinant expression vector comprises an encoding gene for HD-ZIP transcription factor ArHDZ19 of *Anoectochilus roxburghii* 'Hongxia', wherein the nucleotide sequence for the encoding gene is SEQ ID NO: 1 and an amino acid sequence of the encoded HD-ZIP transcription factor ArHDZ19 is SEQ ID NO: 2.

2. The transgenic plant according to claim 1, wherein the transgenic plant is transformed using a recombinant expression vector pHB-ArHDZ19, wherein the recombinant expression vector pHB-ArHDZ19 is formed by ligating, into a pHB binary transformation vector, an ArHDZ19 nucleic acid fragment having BamHI and SpeI restriction sites introduced on two sides of a full-length gene sequence.

3. A method for promoting reproductive growth of the *Anoectochilus roxburghii* 'Hongxia', comprising:

(a) constructing a recombinant expression vector pHB-ArHDZ19 comprising the nucleotide sequence of SEQ ID NO: 1 encoding the HD-ZIP transcription factor ArHDZ19 having the amino acid sequence of SEQ ID NO: 2;

(b) transforming *Anoectochilus roxburghii* 'Hongxia' with the recombinant expression vector;

(c) cultivating the transformed *Anoectochilus roxburghii* 'Hongxia'; and (d) screening and selecting transgenic *Anoectochilus roxburghii* 'Hongxia' plants that comprise the recombinant expression vector or an integrated nucleic acid comprising the nucleotide sequence of SEQ ID NO: 1.

4. The transgenic plant of claim 1, wherein the transgenic plant has increased plant height, increased seed length, increased seed width, and increased seed hundred-grain weight relative to a control plant cultivated under the same conditions.

5. The transgenic plant of claim 1, wherein the transgenic plant is *Arabidopsis thaliana*.

6. The method of claim 3, further comprising:

(e) harvesting seeds produced by the selected transgenic *Anoectochilus roxburghii* 'Hongxia' plants; and (f) screening the harvested seeds for increased seed vitality by determining a seed length, a seed width, and a seed hundred-grain weight, and selecting seeds having an increased seed length, seed width, and seed hundred-grain weight as compared to seeds from a non-transgenic *Anoectochilus roxburghii* 'Hongxia' control plant cultivated under the same conditions.

* * * * *

SEQUENCE LISTING

```
Sequence total quantity: 8
SEQ ID NO: 1            moltype = DNA  length = 2553
FEATURE                 Location/Qualifiers
source                  1..2553
                        mol_type = other DNA
                        organism = Anoectochilus sp.
SEQUENCE: 1
atggcgatgg tggggaagga aggaaaatcc cagcagcatg agctgcagca tattgatgca  60
ggtaagtacg ttaggtatac gccggagcaa gtggaggctc ttgagagggt ttatatggag  120
tgtccaaagc cgagctcact gaggaggcag cagctcatca gagagtgccc gattctctct  180
aacatcgagc ccaagcagat caaagtctgg ttccagaacc ggaggtgtcg tgagaagcag  240
aggaaagagg cttctcgtct ccagacagtt aacagaaagc tttctgctat gaacaagttg  300
```

-continued

```
ctgatggagg agaatgaccg attgcaaaag caagtgtccc acttggttta tgagaatgga  360
tgcatgcgtc aacagattca tactccatct gcgacaacta ctgacactag ctgcgagtct  420
gtagtaacta gtggcccgca caaacaacaa caaaatacaa aattgcagca tcttcaaaga  480
gatgctaaca acccagcagg tctacttgct atagccgagg agaccctatc cgagtttctt  540
tcaaaggcca ctggaacttc tgtcgaatgg gttcagatgg ttggaatgaa gcctggtccg  600
gattctattg gaatcatcgc tgtttcacac aactgcagtg gtgtggcagc acgtgcttgc  660
ggtcttgtga gcttagagcc cacaaaggtt gcggagattc tcaaagcacg cccatcttgg  720
tatcgtgatt gtaggtgcct aaatgtagcg acagtgatcc ctgccggaaa tggagggaat  780
attgagctta tatatatgca gacatatgca cctacaactc ttgcagcggc tcgagatttt  840
tggacactca gatacaccac aggtcttgaa gatggaagtc ttgtgatttg tgagaggtcg  900
ttgacttctt caacaggtgg ccctactggc ccccctgctc tgaactttgt tagggcagaa  960
atgcttccta gtgggtacct tataagaccg tgcgagggtg gtggctcaat gattcacatt  1020
gttgatcatg ttgattggga tgttatgagt gtgcccgaag ttctaaggcc actgtacgaa  1080
tcaccaaaga ttatggcaca taagatgaca atttctgcat tacggtattt gaggcaaatt  1140
gcacatgaga caagtggtga atttgcttac aatagtggtc gtcaacccgc tgttttgagg  1200
acttttagtc agaggttgag cagaggcttc aacgatgcta taaatggatt catggatgat  1260
ggatggtctt taatgagcag tgatggtgga gatgatgtga cagtaactat taattcttcc  1320
tcaagtaaac ttgtgggttc tgtgaattca tcccctctct ttgcctttgg tggtggtatc  1380
ttgtgtgcaa aggcttctat gttgctccag aatgttccac ctgctttact tgttcgtttt  1440
ctgagggaac atcgttctga gtgggctgaa tgtggagtgg atgcatattc tcctgcatca  1500
cttagagaca gctcccatcc catcttaggt gcgagagctg gtggcagctt tcatggcggt  1560
caagttattc taccccttgc acaaactgtg gaaaatgaag agttcttgga ggtgatcaga  1620
cttgaaggcc atgaattttg ccctgacaat gtagccaggg acacttatct attgcagctg  1680
tgcaatggag ttgatgagaa tgctactggt gcatgctctc agcttgtttt tgccccccatt  1740
gatgaatctt ttgcagataa tgcccctttg cttccttctg gttttcgtgt aatcccagtt  1800
gaatctaaaa cagaggtgca tgcagctgcc agaactcttg accttgcatc tactttagaa  1860
gtaggttcag gtggtgcgac gcgccccaac agtgagggtg cctcaactac atctaacttg  1920
agatctgtct tgactatagc attccaattc acatatgaga atcattatcg cgaaaatatg  1980
gcagcaatgg ctcggcaata tgttcgcagc attgtggctt cagtacagag ggttgccatg  2040
gccatctctc cttcacgcgt gggttcgctt ggttcaaaac atttaactgg gtcccctgag  2100
ggtctcactt tagcgcgctg gatttcctgc agttacaagt ttcatactgg cgccgatctc  2160
tttcgttccg agcccgatgt cgagcctcaa gcgggtgatt ctttactgaa gaccctgtgg  2220
cattatcctg atgcaattat gtgctgcact ctgaaggcgt cgcccatgtt tacatttgca  2280
aatcaggcag gccttgacat gctcgaaacc acactcatcg ctcttcagga cataacgctc  2340
gagaagattc tcaatgacag tggccgcaag gtttttgta ctgaattctc taaaatcatg  2400
cagcagggat ttgcttatct gcctggtggg gtatgcctat cgagcatggg taggcctgca  2460
tcttacgatc aggttgtcgc gtggaaggtc cttgatgatg aggacactca tcattgcttg  2520
gccttcatgt tcatgaactg gtcatttgtc taa                             2553

SEQ ID NO: 2           moltype = AA  length = 850
FEATURE                Location/Qualifiers
source                 1..850
                       mol_type = protein
                       organism = Anoectochilus sp.
SEQUENCE: 2
MAMVGKEGKS QQHELQHIDA GKYVRYTPEQ VEALERVYME CPKPSSLRRQ QLIRECPILS  60
NIEPKQIKVW FQNRRCREKQ RKEASRLQTV NRKLSAMNKL LMEENDRLQK QVSHLVYENG  120
CMRQQIHTPS ATTTDTSCES VVTSGPHKQQ QNTKLQHLQR DANNPAGLLA IAEETLSEFL  180
SKATGTSVEW VQMVGMKPGP DSIGIIAVSH NCSGVAARAC GLVSLEPTKV AEILKARPSW  240
YRDCRCLNVA TVIPAGNGGN IELIYMQTYA PTTLAAARDF WTLRYTTGLE DGSLVICERS  300
LTSSTGGPTG PPALNFVRAE MLPSGYLIRP CEGGGSMIHI VDHVDWDVMS VPEVLRPLYE  360
SPKIMAHKMT ISALRYLRQI AHETSGEFAY NSGRQPAVLR TFSQRLSRGF NDAINGFMDD  420
GWSLMSSDGG DDVTVTINSS SSKLVGSVNS SPLFAFGGGI LCAKASMLLQ NVPPALLVRF  480
LREHRSEWAE CGVDAYSPAS LRDSSHPILG ARAGGSFHGG QVILPLAQTV ENEEFLEVIR  540
LEGHEFCPDN VARDTYLLQL CNGVDENATG ACSQLVFAPI DESFADNAPL LPSGFRVIPV  600
ESKTEVHAAA RTLDLASTLE VGSGGATRPN SEGASTTSNL RSVLTIAFQF TYENHYRENM  660
AAMARQYVRS IVASVQRVAM AISPSRVGSL GSKHLTGSPE GLTLARWISC SYKFHTGADL  720
FRSEPDVEPQ AGDSLLKTLW HYPDAIMCCT LKASPMFTFA NQAGLDMLET TLIALQDITL  780
EKILNDSGRK VFCTEFSKIM QQGFAYLPGG VCLSSMGRPA SYDQVVAWKV LDDEDTHHCL  840
AFMFMNWSFV                                                        850

SEQ ID NO: 3           moltype = DNA  length = 37
FEATURE                Location/Qualifiers
source                 1..37
                       mol_type = other DNA
                       organism = synthetic construct
SEQUENCE: 3
tcggtacccg gggatccatg gcgatggtgg ggaagga                           37

SEQ ID NO: 4           moltype = DNA  length = 38
FEATURE                Location/Qualifiers
source                 1..38
                       mol_type = other DNA
                       organism = synthetic construct
SEQUENCE: 4
tgctcaccat gtcgacgaca aatgaccagt tcatgaac                          38

SEQ ID NO: 5           moltype = DNA  length = 20
FEATURE                Location/Qualifiers
```

-continued

```
source                  1..20
                        mol_type = other DNA
                        organism = synthetic construct
SEQUENCE: 5
gtatacgccg gagcaagtgg                                                         20

SEQ ID NO: 6            moltype = DNA  length = 20
FEATURE                 Location/Qualifiers
source                  1..20
                        mol_type = other DNA
                        organism = synthetic construct
SEQUENCE: 6
tctctgatga gctgctgcct                                                         20

SEQ ID NO: 7            moltype = DNA  length = 20
FEATURE                 Location/Qualifiers
source                  1..20
                        mol_type = other DNA
                        organism = synthetic construct
SEQUENCE: 7
gctagtggcc gtacaactgg                                                         20

SEQ ID NO: 8            moltype = DNA  length = 20
FEATURE                 Location/Qualifiers
source                  1..20
                        mol_type = other DNA
                        organism = synthetic construct
SEQUENCE: 8
gccagcaagg tccaatcgaa                                                         20
```